United States Patent
Li et al.

(10) Patent No.: US 8,838,240 B2
(45) Date of Patent: Sep. 16, 2014

(54) HEMODYNAMIC STATUS ASSESSMENT DURING TACHYCARDIA

(75) Inventors: Dan Li, Shoreview, MN (US); Krzysztof Siejko, Maple Grove, MN (US); Abhilash Patangay, Inver Grove Heights, MN (US)

(73) Assignee: Cardiac Pacemakers Inc., St. Paul, MN (US)

( * ) Notice: Subject to any disclaimer, the term of this patent is extended or adjusted under 35 U.S.C. 154(b) by 1441 days.

(21) Appl. No.: 12/283,234

(22) Filed: Sep. 10, 2008

(65) Prior Publication Data
US 2009/0131999 A1 May 21, 2009

Related U.S. Application Data

(60) Provisional application No. 61/003,941, filed on Nov. 21, 2007.

(51) Int. Cl.
| | | |
|---|---|---|
| A61N 1/36 | (2006.01) | |
| A61N 1/368 | (2006.01) | |
| A61B 5/0464 | (2006.01) | |
| A61N 1/365 | (2006.01) | |

(52) U.S. Cl.
CPC ......... *A61N 1/36585* (2013.01); *A61N 1/36564* (2013.01); *A61N 1/36578* (2013.01); *A61N 1/36521* (2013.01)
USPC .................. 607/17; 607/14; 607/15; 600/518

(58) Field of Classification Search
USPC .......................... 607/14, 15, 17; 600/513–518
See application file for complete search history.

(56) References Cited

U.S. PATENT DOCUMENTS

| | | | |
|---|---|---|---|
| 6,221,011 B1 | 4/2001 | Bardy | |
| 6,270,457 B1 | 8/2001 | Bardy | |
| 6,277,072 B1 | 8/2001 | Bardy | |
| 6,280,380 B1 | 8/2001 | Bardy | |
| 6,312,378 B1 | 11/2001 | Bardy | |
| 6,336,903 B1 | 1/2002 | Bardy | |
| 6,358,203 B2 | 3/2002 | Bardy | |
| 6,368,284 B1 | 4/2002 | Bardy | |
| 6,398,728 B1 | 6/2002 | Bardy | |
| 6,440,066 B1 | 8/2002 | Bardy | |
| 6,959,214 B2 | 10/2005 | Pape et al. | |
| 7,082,330 B2 | 7/2006 | Stadler et al. | |
| 7,336,994 B2 * | 2/2008 | Hettrick et al. | 607/5 |
| 2003/0014083 A1 * | 1/2003 | Kupper | 607/9 |
| 2005/0027323 A1 | 2/2005 | Mulligan | |
| 2007/0249945 A1 * | 10/2007 | Li et al. | 600/515 |

FOREIGN PATENT DOCUMENTS

| | | |
|---|---|---|
| EP | 1345651 | 3/2006 |
| WO | WO 2005/028029 | 3/2005 |

\* cited by examiner

*Primary Examiner* — Tammie K Heller
(74) *Attorney, Agent, or Firm* — Brooks, Cameron & Huebsch, PLLC

(57) ABSTRACT

Systems and methods provide for sensing, during an event of tachycardia, hemodynamic signals concurrently from at least two spatially separated locations within a patient, and quantifying a spatial relationship between the hemodynamic signals. Hemodynamic stability or state of the patient during the tachycardia event is determined based at least in part on the quantified spatial relationship. One or more anti-tachycardia therapies to treat the tachycardia may be selected based at least in part on the determined stability or state of patient hemodynamics, and the selected one or more anti-tachycardia therapies may be delivered to treat the tachycardia. The hemodynamic signals may comprise at least two, or a mixed combination, of cardiac impedance signals, cardiac chamber pressure signals, arterial pressure signals, heart sounds; and acceleration signals.

23 Claims, 9 Drawing Sheets

HEMODYNAMIC STATUS ASSESSMENT DURING TACHYCARDIA

RELATED APPLICATIONS

This application claims the benefit of Provisional Patent Application Ser. No. 61/003,941 filed on Nov. 21, 2007, to which priority is claimed pursuant to 35 U.S.C. §119(e) and which is hereby incorporated herein by reference in its entirety.

FIELD OF THE INVENTION

The present invention relates generally to evaluating patient hemodynamics, and more specifically, to assessing a patient's hemodynamic status during a tachycardia event based on a spatial relationship between hemodynamic signals acquired by a multiplicity of distributed hemodynamic sensors.

BACKGROUND OF THE INVENTION

Proper cardiac function relies on the synchronized contractions of the heart at regular intervals. When normal cardiac rhythm is initiated at the sinoatrial node, the heart is said to be in sinus rhythm. However, when the heart experiences irregularities in its coordinated contraction, due to electrophysiologic disturbances caused by a disease process or from an electrical disturbance, the heart is denoted to be arrhythmic. The resulting cardiac arrhythmia impairs cardiac efficiency and can be a potential life threatening event.

Cardiac arrhythmias occurring in the atria of the heart, for example, are called supra-ventricular tachyarrhythmias (SVTs). SVTs take many forms, including atrial fibrillation and atrial flutter. Both conditions are characterized by rapid, uncoordinated contractions of the atria. Besides being hemodynamically inefficient, the rapid contractions of the atria can also adversely effect the ventricular rate. This occurs when the aberrant contractile impulse in the atria are transmitted to the ventricles. It is then possible for the aberrant atrial signals to induce ventricular tachyarrhythmias.

Cardiac arrhythmias occurring in the ventricular region of the heart, by way of further example, are called ventricular tachyarrhythmias. Ventricular tachycardia (VTs), for example, are conditions denoted by a rapid heart beat, 150 to 250 beats per minute, that has its origin in some abnormal location with the ventricular myocardium. The abnormal location typically results from damage to the ventricular myocardium from a myocardial infarction. Ventricular tachycardia can quickly degenerate into ventricular fibrillation (VF). Ventricular fibrillation is a condition denoted by extremely rapid, non synchronous contractions of the ventricles. This condition is fatal unless the heart is returned to sinus rhythm within a few minutes.

Implantable cardioverter/defibrillators (ICDs) have been used as an effective treatment for patients with serious ventricular tachyarrhythmias. ICDs are able to recognize and treat tachyarrhythmias with a variety of therapies. To effectively deliver these treatments, the ICD must first identify the type of tachyarrhythmia that is occurring, after which appropriate therapy may be provided to the heart. An inaccurate identification of a detected tachyarrhythmia by the ICD can result in delivery of a high energy therapy, such as defibrillation therapy, when such therapy is unnecessary.

SUMMARY OF THE INVENTION

The present invention is generally directed to systems and methods for evaluating patient hemodynamics. Systems and methods of the present invention are directed to assessing a patient's hemodynamic status during a tachycardia event using a multiplicity of hemodynamic sensors. Systems and methods of the present invention are further directed to assessing a patient's hemodynamic status during a tachycardia event based on a spatial relationship between hemodynamic signals acquired by a multiplicity of distributed hemodynamic sensors.

According to various embodiments, methods of the present invention involve sensing, during an event of tachycardia, hemodynamic signals concurrently from at least two spatially separated locations within a patient, and quantifying a spatial relationship between the hemodynamic signals. Hemodynamic stability or state of the patient during the tachycardia event is determined based at least in part on the quantified spatial relationship.

In accordance with various embodiments, methods of the present invention involve sensing, during an event of tachycardia, hemodynamic signals concurrently from at least two spatially separated locations within a patient, and quantifying a spatial relationship between the hemodynamic signals. A state of patient hemodynamics during the tachycardia event is determined based at least in part on the quantified spatial relationship. One or more anti-tachycardia therapies to treat the tachycardia may be selected based at least in part on the determined stability or state of patient hemodynamics, and the selected one or more anti-tachycardia therapies may be delivered to treat the tachycardia.

According to further embodiments, implantable systems include at least two hemodynamic sensors adapted for spatially-separated positioning relative to a patient's heart and sensing hemodynamic signals. A lead comprising one or more electrodes is coupled to detection circuitry and energy delivery circuitry. A processor is coupled to the hemodynamic sensors, lead, detection circuitry, and energy delivery circuitry. The processor is configured to sense, during an event of tachycardia, hemodynamic signals concurrently from the hemodynamic sensors, quantify a spatial relationship between the sensed hemodynamic signals, and determine a hemodynamic status of the patient during the tachycardia event based at least in part on the quantified spatial relationship. The processor is configured to deliver one or more anti-tachycardia therapies associated with the hemodynamic status of the patient.

In accordance with other embodiments, systems and methods of the present invention provide for diagnostic assessment of patient hemodynamics, and need not incorporate a therapy delivery facility. Patient hemodynamic assessment implemented by such diagnostic embodiments provides for sensing, during an event of tachycardia, hemodynamic signals concurrently from at least two spatially separated locations within a patient, quantifying a spatial relationship between the hemodynamic signals, and determining hemodynamic stability or state of the patient during the tachycardia event based at least in part on the quantified spatial relationship.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
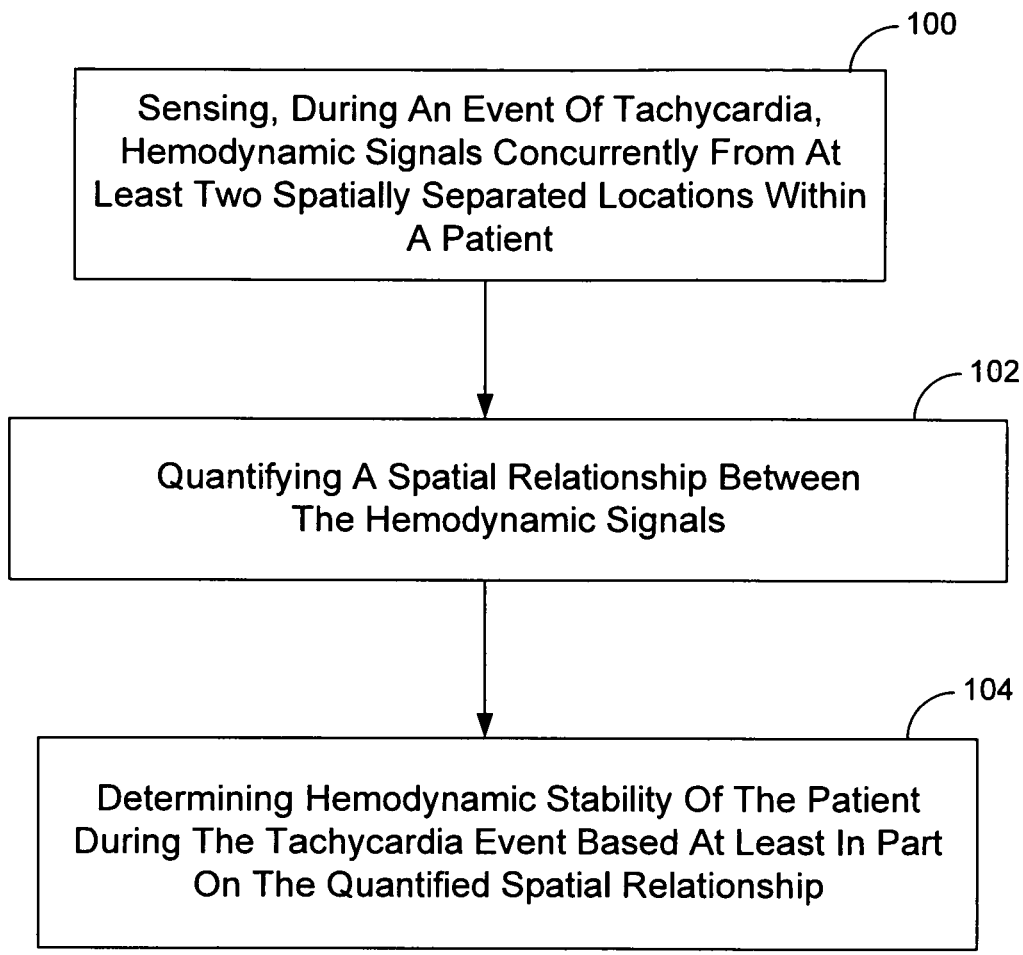
FIG. 1 is a flow diagram showing various processes involving assessment of patient hemodynamics in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described hereinbelow. For example, a device or system may be implemented to include one or more of the features and/or processes described below. It is intended that such device or system need not include all of the features described herein, but may be implemented to include selected features that provide for useful structures and/or functionality. Such a device or system may be implemented to provide a variety of therapeutic or diagnostic functions.

In some configurations, devices or systems of the present invention may be configured for intrathoracic or transvenous deployment or a combination thereof. In other configurations, devices or systems of the present invention may be implanted subcutaneously, but extra-thoracically. In further configurations, systems and devices of the present invention may include some or all components that are configured for cutaneous or patient-external deployment, such as in diagnostic configurations. Accordingly, a wide range of device and system configurations are contemplated.

Delivering the appropriate therapy when needed to treat a cardiac arrhythmia is an important function of an implantable cardiovertor/defibrillator (ICD). To determine the "appropriateness" of a therapy to treat an arrhythmia, an ICD requires accurate and immediate interpretation of the arrhythmia and assessment of patient hemodynamic status. During the arrhythmia, there is change in cardiac synchrony. It is expected that hemodynamically stable and unstable arrhythmias have different levels of impact on cardiac synchrony. Detecting and quantifying the change in cardiac synchrony may help to gauge the hemodynamic outcome during arrhythmia.

It is hypothesized that, compared to normal sinus rhythm, an arrhythmia results in a change in the sound source (or other hemodynamic signal source) as well as the sound (or other hemodynamic signal) propagation through the media between the sound source and the sound sensors (or other hemodynamic sensor). Unlike conventional techniques that focus on the detection of the change of the sound source during arrhythmia (e.g., S1 or S2 heart sound strength, power, duration, or relative timing as a measure of electrical-mechanical coupling), the present invention focuses on detecting a change of the sound or other hemodynamic signal propagation, such as decay rate.

Embodiments of the present invention are directed to systems and methods that provide for hemodynamic stability detection during tachycardia using hemodynamic signals, such as heart sound (HS) signals, from at least two spatially distributed sensors. Typical hemodynamic sensors include accelerometers, microphones, and pressure sensors, among others.

According to embodiments of the present invention, assessing a change in heart sound propagation resulting from cardiac arrhythmia is based on a spatial relationship between the heart sounds signals or other hemodynamic signals collected from two positionally distinct sensors. Features extracted from a spatial relationship analysis, such as the time delay or correlation coefficient for example, can be used to determine the state of patient hemodynamics during tachycardia events, thus providing important information that can be used to facilitate selection of an appropriate or optimal therapy delivery strategy to treat the tachyarrhythmias and to prevent unnecessary delivery of high energy therapies, such as cardioversion and defibrillation therapies.

FIG. 1 is a flow diagram showing various processes involving assessment of patient hemodynamics in accordance with embodiments of the present invention. According to FIG. 1, embodiments of the present invention involve sensing 100, during an event of tachycardia, hemodynamic signals concurrently from at least two spatially separated locations within a patient, and quantifying 102 a spatial relationship between the hemodynamic signals. Hemodynamic stability of the patient is determined 104 during the tachycardia event based at least in part on the quantified spatial relationship.

Figure 2:
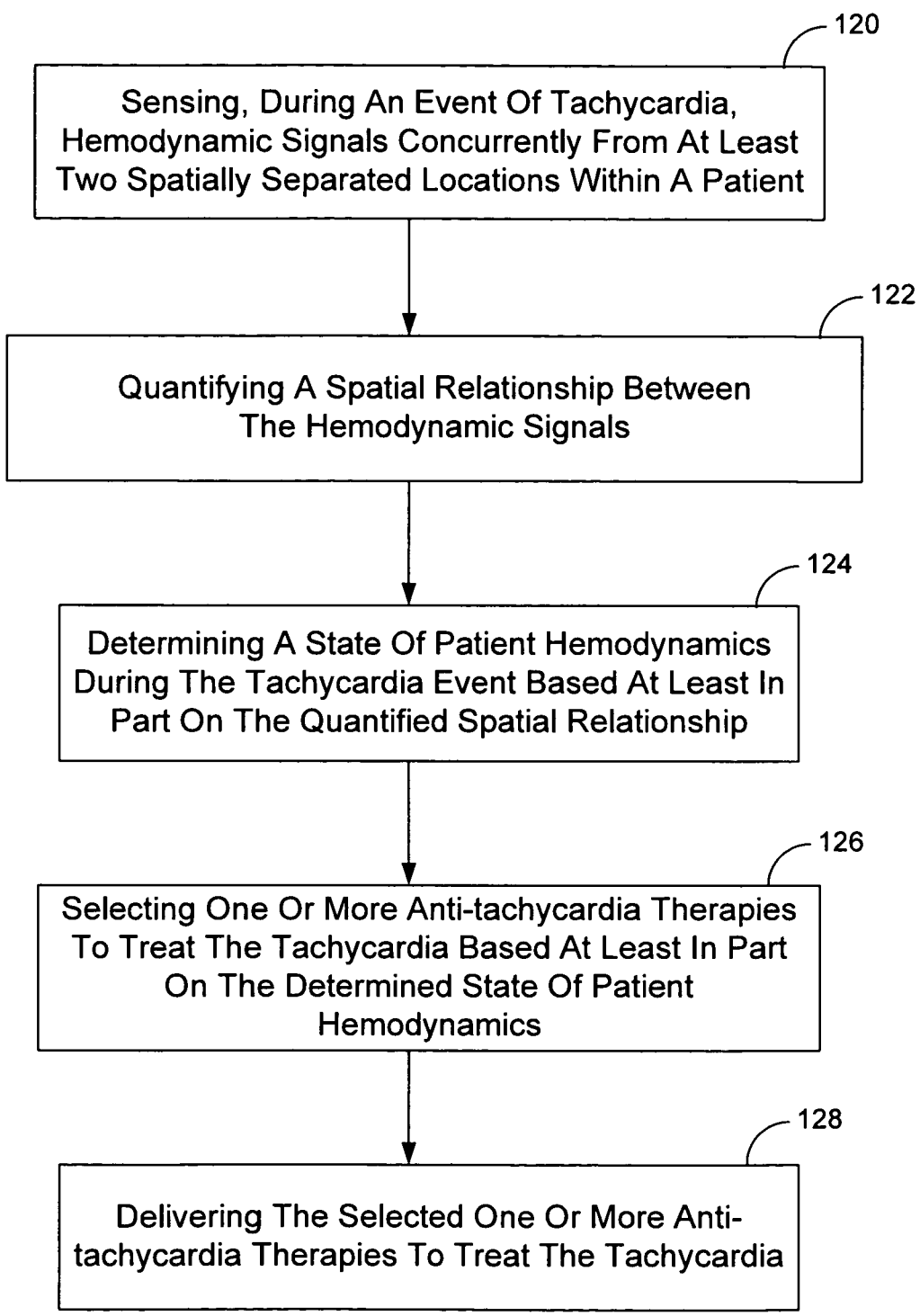
FIG. 2 is a flow diagram showing various processes involving assessment of patient hemodynamics in accordance with other embodiments of the present invention.

FIG. 2 is a flow diagram showing various processes involving assessment of patient hemodynamics in accordance with other embodiments of the present invention. According to FIG. 2, embodiments of the present invention involve sensing 120, during an event of tachycardia, hemodynamic signals concurrently from at least two spatially separated locations within a patient, and quantifying 122 a spatial relationship between the hemodynamic signals. Embodiments according to FIG. 2 further provide for determining 124 a state of patient hemodynamics during the tachycardia event based at least in part on the quantified spatial relationship, and selecting 126 one or more anti-tachycardia therapies to treat the tachycardia based at least in part on the determined state of patient hemodynamics. The selected one or more anti-tachycardia therapies may be delivered 128 to treat the tachycardia.

Embodiments of the present invention employ distributed heart sound sensing for assessing a patient's hemodynamic status based on a spatial relationship between heart sounds signals. The opening and closing of the patient's heart valves during a heartbeat causes high-frequency vibrations in the adjacent heart wall and blood vessels. These vibrations can be sensed in the patient's body as heart sounds, and may be detected by sensors. A phonocardiogram (PCG) transducer, for example, may be implanted within a patient and converts acoustical energy of the heart sounds to electrical energy, resulting in a PCG waveform 120 that may be recorded, processed, and/or displayed, as shown by the graph in the upper portion of FIG. 3.

Figure 3:
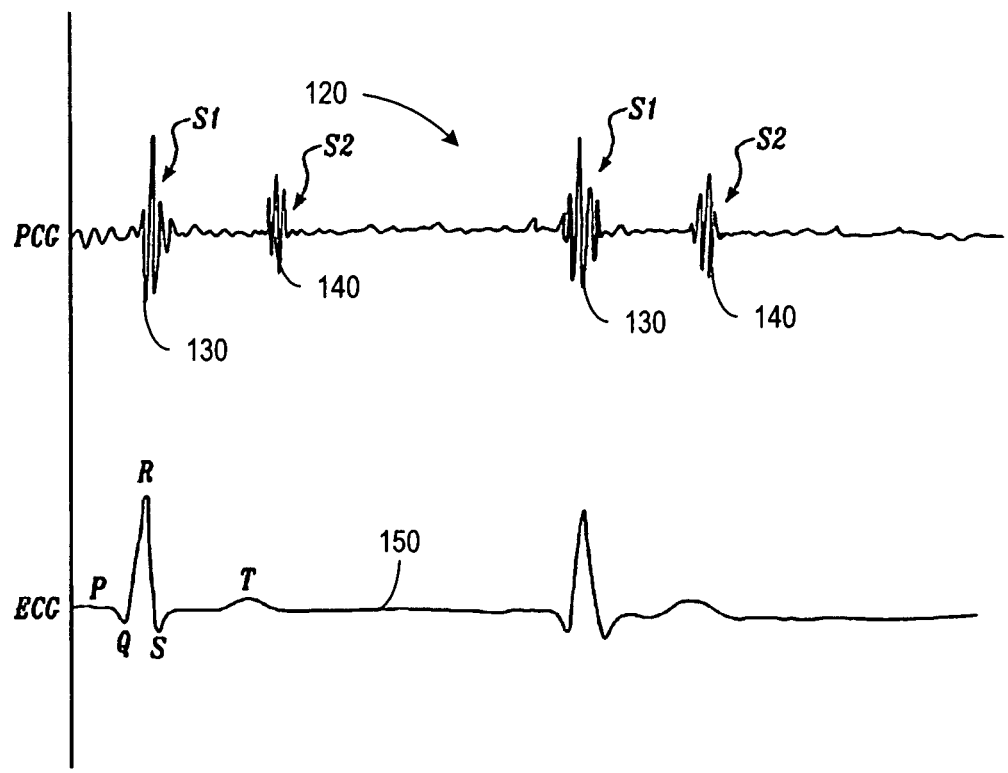
FIG. 3 is a pictorial diagram of a phonocardiogram (PCG) waveform and an electrocardiogram (ECG) waveform for two consecutive heartbeats.

As indicated by the PCG waveform 120 shown in FIG. 3, a typical heartbeat produces two main heart sounds. A first heart sound 130, denoted S1, is generated by vibration generally associated with the closure of the tricuspid and mitral valves at the beginning of systole. Typically, the heart sound 130 is about 14 milliseconds long and contains frequencies up to approximately 500 Hz. A second heart sound 140, denoted S2, is generally associated with vibrations resulting from the closure of the aortic and pulmonary valves at the end of systole. While the duration of the second heart sound 140 is typically shorter than the first heart sound 130, the spectral bandwidth of the second heart sound 140 is typically larger than that of the first heart sound 130.

An electrocardiogram (ECG) waveform 150 describes the electrical activity of a patient's heart. The graph in the lower portion of FIG. 3 illustrates an example of the ECG waveform 150 for two heartbeats and corresponds in time with the PCG waveform 120 also shown in FIG. 3. Referring to the first shown heartbeat, the portion of the ECG waveform 150 representing depolarization of the atrial muscle fibers is referred to as the "P" wave. Depolarization of the ventricular muscle fibers is collectively represented by the "Q," "R," and "S" waves of the ECG waveform, referred to as the QRS complex. Finally, the portion of the waveform 150 representing repolarization of the ventricular muscle fibers is known as the "T" wave. Between heartbeats, the ECG waveform 150 returns to an isopotential level.

According to embodiments of the present invention, two or more sensors may be activated within a patient to collect heart sounds signals when certain events occur (event triggered) or when a command is issued (command triggered). In one embodiment, two heart sounds sensors, HS1 and HS2, may be deployed across the chest (externally or, more preferably, internally), implanted through the cardiovascular system or embedded subcutaneously. Heart sounds sensors may be placed closer to the apex region and aorta region of the heart to obtain a higher signal to noise ratio for the respective heart sound components, S1 and S2.

The two sensors, HS1 and HS2, can be physically identical sensors, or they can be of different types. Examples of heart sounds sensors include accelerometers that sense vibrations, microphones that sense sound pressure levels, and other types of sensors (such as pressure sensors) from which a heart sounds signal may be extracted, typically through some pre-processing techniques such as bandpass filtering or source separation. In one embodiment, HS1 may be implemented as an in- or on-can accelerometer, and HS2 may be configured as a lead-mounted (i.e., RV or LV lead) pressure sensor that provides the desired heart sounds signal, typically through filtering.

Figure 4:
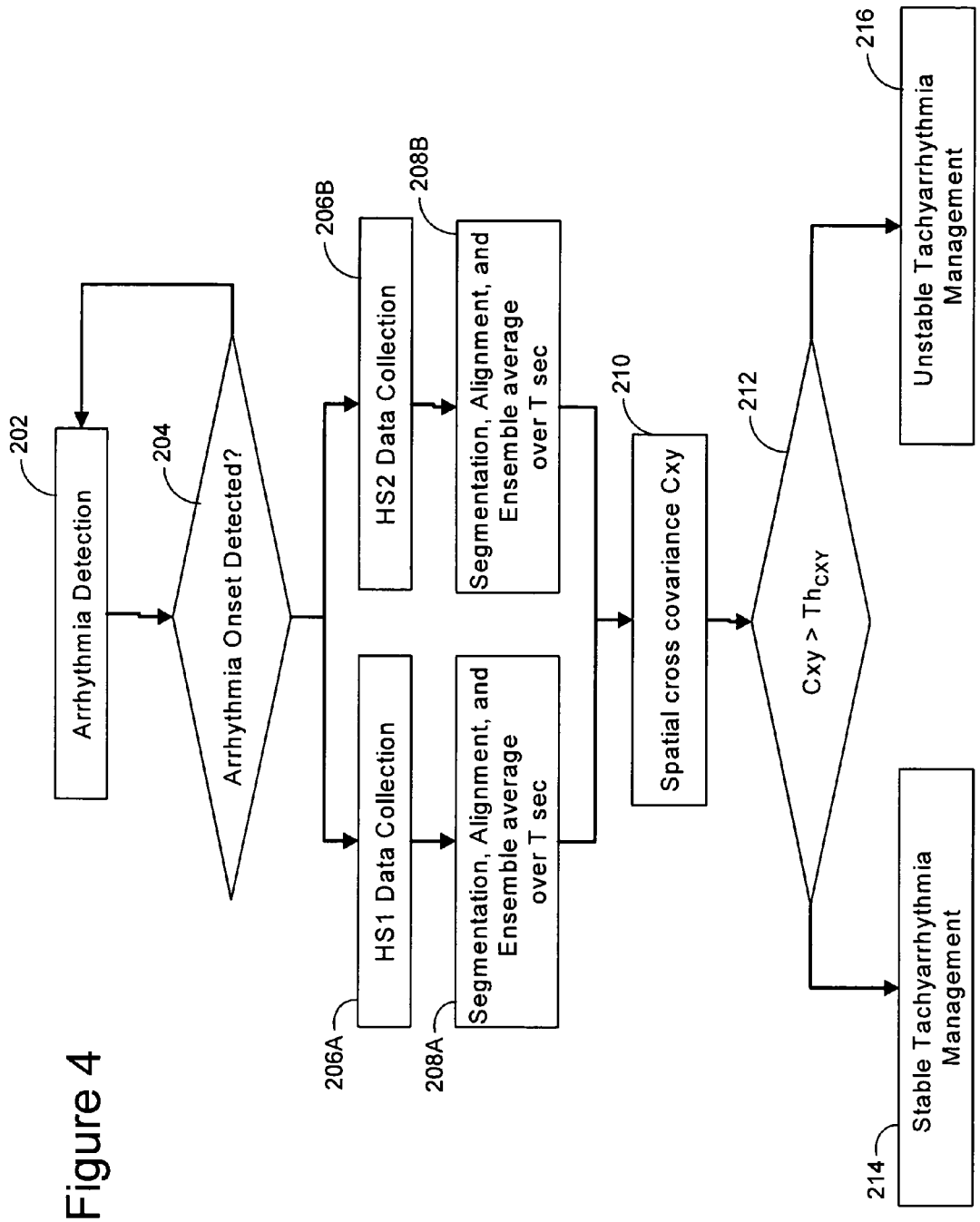
FIG. 4 is a flow diagram of an algorithm that uses the cross-covariance between heart sounds signals acquired by spatially separated heart sounds sensors to differentiate stable from unstable arrhythmias and deliver appropriate therapies in accordance with embodiments of the present invention.

FIG. 4 is a flow diagram of an algorithm that uses the cross-covariance between heart sounds signals acquired by spatially separated heart sounds sensors to differentiate stable from unstable arrhythmias and deliver appropriate therapies in accordance with embodiments of the present invention. As is shown in FIG. 4, when an arrhythmia onset is detected 202, 204, the heart sounds sensors (HS1 and HS2) concurrently collect 206A, 206B heart sounds signals for a preset period of time T. Preferably, the heart sounds sensors HS1, HS2 are activated (i.e., energized) when needed, typically upon detection 202, 204 of an arrhythmia. Heart sounds signals during period T may be segmented and aligned relative to the R-wave detected during arrhythmia, and ensemble-averaged 208A, 208B over time period T. The ensemble-averaged heart signal acquired from both heart sounds sensors, HS1 and HS2, are compared to derive one or more mathematical indices or metrics that quantify the relationship between the responses to the arrhythmia from the spatially distributed heart sounds sensors. In another embodiment, heart sound segment-wise analysis, rather than performing ensemble averaging first and then looking for a cross relationship, may be used to track the changes of the spatial relationships between two or more heart sounds sensors.

According to the embodiment of FIG. 4, the spatial relationship between heart sounds signals acquired by the heart sounds sensors, HS1 and HS2, can be characterized by using a cross-covariance or correlation method 210. The maximum correlation, Cxy, between the heart sound sensor signals can be found within a specified range of time lag, and used to describe the relationship between the heart sound sensor responses. In addition to cross-covariance and cross-correlation, other methods can also be used to quantify the spatial relationship between the heart sound sensor responses. Examples include cross-spectra or coherence, mutual information or cross-entropy, among others.

Quantification of the spatial relationship between heart sound sensor signals may be used to determine, or track, a patient's hemodynamic status during an arrhythmia. In one embodiment, one or more threshold values of the spatial relationship between heart sound sensor signals (SR-HS) may be used to determine the patient's hemodynamic stability, such as from a number of predetermined discrete levels (e.g., x % of the baseline SR-HS value). For example, the spatial cross-covariance, Cxy, computed in block 210, may be compared 212 to a threshold, $Th_{CXY}$. The threshold, $Th_{CXY}$, is preferably a threshold established in relation to a normal hemodynamic state of the patient, such as during normal sinus rhythm. The comparison 212 of the cross-covariance, Cxy, to a threshold established in relation to a normal hemodynamic state is important because it establishes the "normal" values for a specific patient with his/her specific heart sound sensor deployment.

After a hemodynamic status level is determined for the patient, an anti-arrhythmia therapy associated with that hemodynamic status level during arrhythmia can be delivered. In one embodiment, if the detected tachycardia is deemed hemodynamically stable, as can be determined by the comparison performed in block 212, then a tachyarrhythmia management strategy appropriate for treating hemodynamically stable arrhythmias may be implemented 214. If the detected tachycardia is deemed hemodynamically unstable, then a tachyarrhythmia management strategy appropriate for treating hemodynamically unstable arrhythmias may be implemented 216.

By way of example, anti-tachycardia pacing (ATP) can be delivered, and/or the arrhythmia sustained duration timer can be extended, as part of a tachyarrhythmia management therapy strategy 214 appropriate for treating hemodynamically stable arrhythmia. Various forms of ATP therapy that differ in terms of aggressiveness may be selected for delivery based on the relative degree of hemodynamic stability (e.g., ATP-1 for treating tachyarrhythmias of relatively high hemodynamic stability, ATP-2 for treating tachyarrhythmias of relatively low hemodynamic stability, where ATP-2 is more aggressive than ATP-1). Otherwise, defibrillation therapy can be immediately delivered once the hemodynamics associated with an arrhythmia is declared unstable, based on SR-HS measures, as part of a tachyarrhythmia management therapy strategy 216 appropriate for treating hemodynamically unstable arrhythmias.

Assessing patient hemodynamics based on an SR-HS in accordance with the present invention can also be used post therapy to evaluate whether the therapy delivered to the patient was effective in recovering patient hemodynamics. By using hemodynamic status tracking according the present invention, the implantable device can decide whether another therapy is needed or would be more effective if it is determined that SR-HS values are not recovering to a "normal" value within a certain duration of time.

As previously discussed, two or more heart sounds sensors are used to acquire heart sounds signals from which quantification of a spatial relationship between heart sounds signals may be determined in accordance with the present invention. Systems and methods of the present invention may employ a broad scope of sensor modalities and sensor signals that represent the cardiac hemodynamics during arrhythmias, in addition to heart sounds. Hemodynamic signals may be acquired using multiple sensors of the same modality, or different modality, for stable and unstable arrhythmia differentiation. Suitable hemodynamic sensors include various types of cardiac impedance sensors, pressure sensors, accelerometers, and microphones, among others. For example, two different cardiac impedance (Z) vectors may be used, such as an RV tip-to-coil vector and an LV tip-to-can vector. Two different pressure sensors or pressure sensor measurements may be used, such as one being a lead-based RV pressure sensor or measurement and the other being a wireless pulmonary arterial (PA) pressure sensor or measurement. Mixed sensors may be used, such as one acoustic or motion sensor (e.g., accelerometer) and one cardiac impedance sensor. A myriad of sensor and sensor signals, and combinations thereof, are contemplated.

The following is an illustrative example of hemodynamic stability assessment in accordance with embodiments of the present invention. This example summarizes a preclinical animal (swine) study in which two accelerometers were placed on the chest surface, one at the aorta region and the other at the apex region. The accelerometers were used to record heart sounds signals simultaneously along with Gems and intracardiac pressures during induced ventricular tachycardia (VT) and ventricular fibrillation (VF) episodes. Using a cross-covariance method, such as that illustrated in FIG. 4, the maximum cross-covariance between the ensemble-averaged heart sounds from the two accelerometers was computed during normal sinus rhythm (NSR), VT, and VF.

Ventricular tachycardia is further separated into hemodynamically stable and unstable VT using the following description. If the mean aortic pressure (MAoP) during the first two seconds of VT is >50% of the baseline MAoP, then this VT episode is considered hemodynamically stable. Otherwise, this VT episode is considered hemodynamically unstable.

An example of the heart sounds recordings from the two accelerometers during NSR, stable VT, unstable VT, and VF is provided in FIGS. 5A-5D, respectively. FIGS. 5A-5D show a heart sounds recording signal 250 obtained from an accelerometer positioned at the apex of the heart, and another heart sounds recording signal 252 positioned at the aorta. Also shown is an EGM signal 254 obtained from a right ventricular lead electrode. The peak of the R-wave of the EGM signal 254 is denoted by an "X." The peak of the R-wave is used to align the heart sounds signals acquired by the two heart sounds sensors.

Figure 5A:
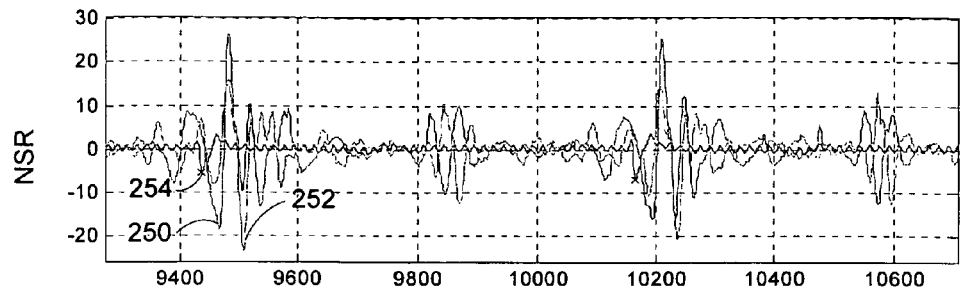
FIGS. 5A-5D pictorially demonstrate how two heart sounds signals correlate with one another for each of four cardiac scenarios, including normal sinus rhythm, stable ventricular tachycardia, unstable ventricular tachycardia, and ventricular fibrillation.
Figure 5B:
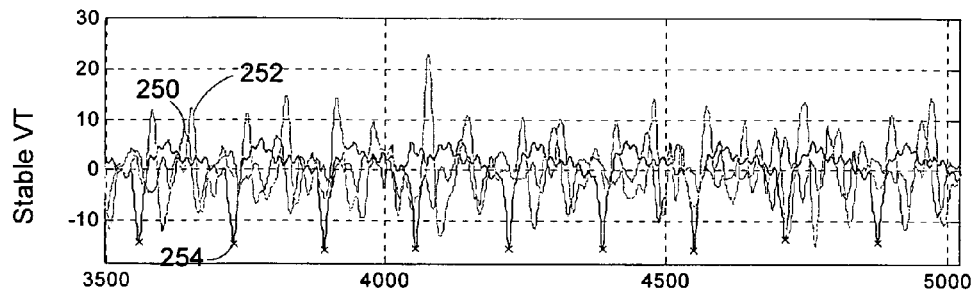
Figure 5C:
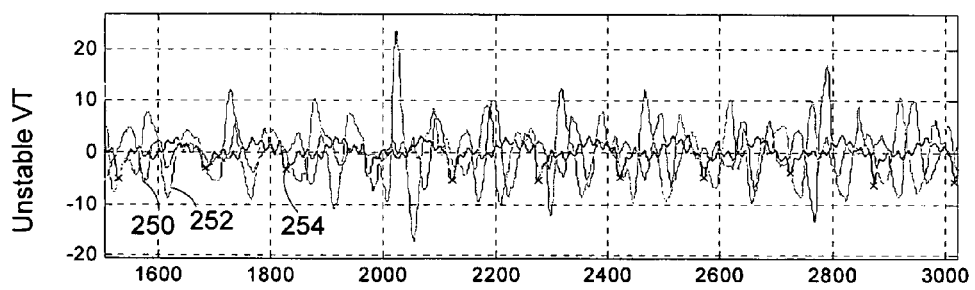
Figure 5D:
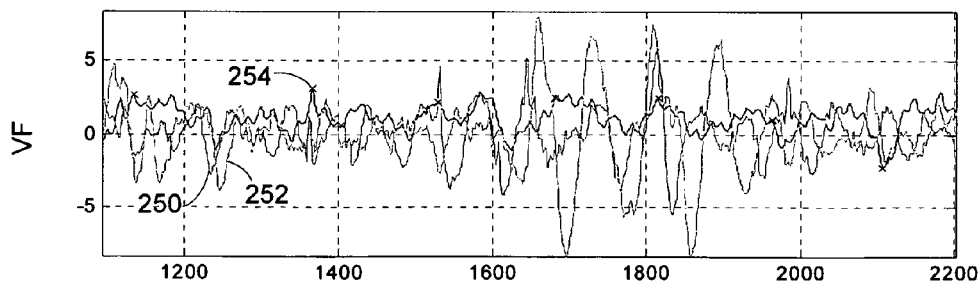

FIGS. 5A-5D pictorially demonstrate how the two heart sounds signals correlate with one another for each of the four cardiac scenarios depicted. In particular, the response of the two heart sounds signals 250 and 252 are very well correlated during normal sinus rhythm, as can be seen in FIG. 5A. The response characteristics of the heart sounds sensors are quite similar in the NSR scenario, indicating that the characteristics of the heart sounds propagating in the media between the heart (source) and the two sensors are very similar (i.e., strongly correlated). The response characteristics of the heart sounds sensors are somewhat similar in the stable VT scenario, as shown in FIG. 5B, indicating that signals corresponding to the heart sounds propagating in the media between the heart and the two sensors during a stable VT episode are less strongly correlated than in the NSR scenario, but sufficiently correlated to distinguish a stable VT episode from an unstable VT or VF scenario, as can be seen in FIGS. 5C and 5D, respectively.

Figure 6:
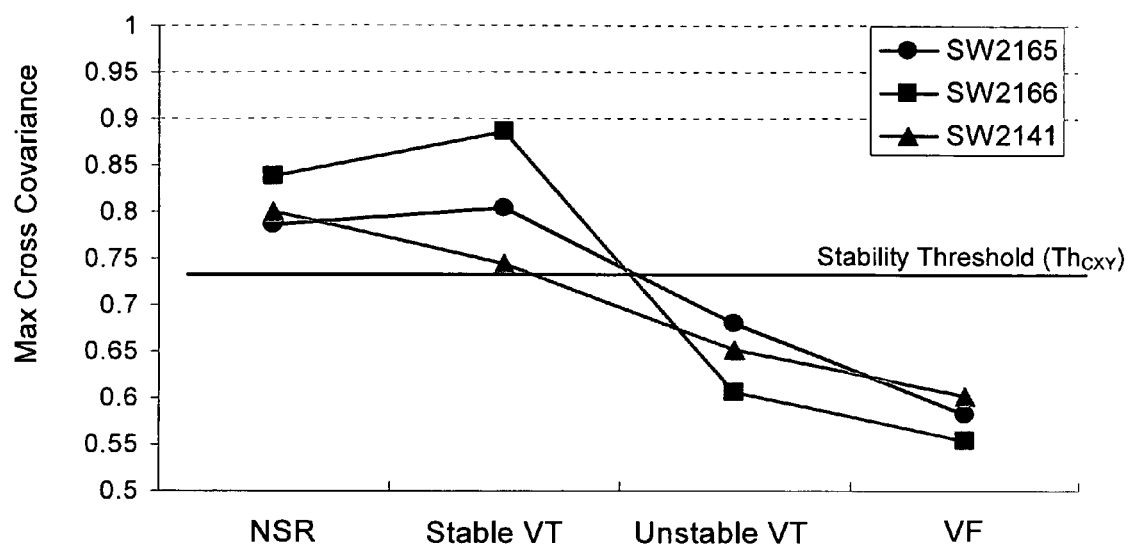
FIG. 6 is a plot of maximum cross-covariance between heart sounds signals developed using heart sounds sensors positioned at the aorta and apex for normal sinus rhythm and different types of tachyarrhythmias in accordance with embodiments of the present invention.

FIG. 6 is a plot of maximum cross-covariance between heart sounds signals developed using the heart sounds sensors positioned at the aorta and apex as discussed above. FIG. 6 shows the maximum cross-covariance of the two heart sound sensor responses during NSR and different types of tachyarrhythmias for three subject animals.

In FIG. 6, the maximum cross-covariance of the ensemble-averaged heart sounds segment processed from three animals indicate a clear deterioration of spatial correlation when the arrhythmia becomes hemodynamically unstable. A stability threshold is shown in FIG. 6, which represents a predetermined delineation between stable and unstable tachyarrhythmia (see, e.g., block 212 of FIG. 4, where Cxy is compared to $Th_{CXY}$). With more episodes and more animals from the study being analyzed, accumulative results clearly demonstrate that spatial correlation is statistically smaller during unstable VT and VF, compared to stable VT.

Figure 7:
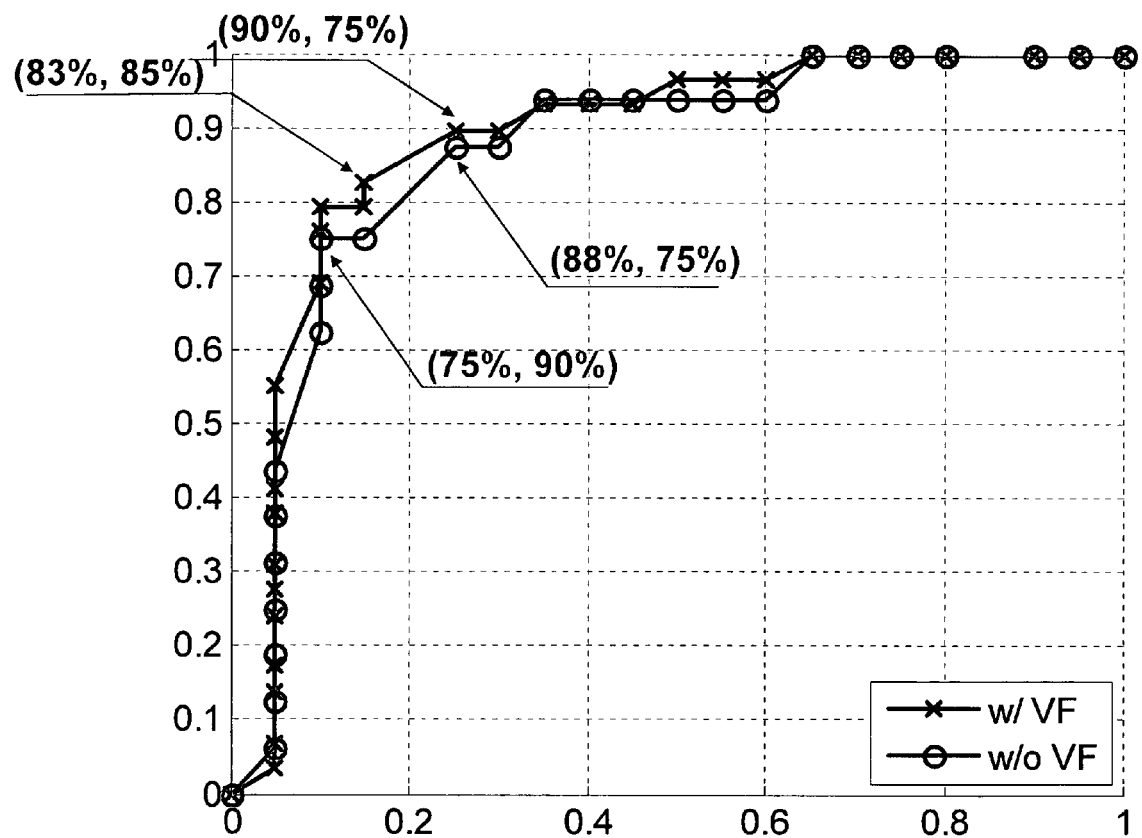
FIG. 7 shows a plot of specificity (1-specificity) versus sensitivity for hemodynamic status assessment in accordance with embodiments of the present invention.

FIG. 7 shows a Receiver Operating Characteristic (ROC) curve that depicts the sensitivity (in the y-axis) and 1-specificity (or, false alarm rate, in the x-axis) for detecting the hemodynamically stable ventricular tachyarrhythmias, in accordance with the present invention. Sensitivity refers to the ability of an algorithm to correctly identify hemodynamically stable arrhythmias. Specificity refers to the ability of an algorithm to correctly identify hemodynamically unstable arrhythmias. The higher the specificity, the lower the false positives. The plots shown in FIG. 7 are representative of the ratio of maximum cross-covariance with respect to baseline (with and without VF), which may be determined by adjusting the stability threshold, $Th_{CXY}$.

Adjusting the stability threshold, $Th_{CXY}$, results in a change in the curves shown in FIG. 7. As such, the stability threshold, $Th_{CXY}$, may be selected to achieve a desired level of specificity and sensitivity for distinguishing between stable and unstable tachyarrhythmias/hemodynamic states. For example, the stability threshold, $Th_{CXY}$, may be selected to achieve a relatively high sensitivity and a moderately high specificity, such as a sensitivity of 90% and a specificity of 80%.

A hemodynamic status assessment methodology of the present invention may be implemented in a variety of medical diagnostic devices and systems, including implantable and patient-external devices and systems. For example, a hemodynamic status assessment methodology of the present invention may be implemented entirely by an implanted device (e.g., pacemaker, ICD, CRT device, cardiac monitoring device), entirely by a patient-external system, or in a distributed manner by both implanted and patient-external devices or systems. In the context of a patient-external or distributed approach, various external systems may be employed, such as a programmer and/or a networked system, such as an advanced patient management system.

Figure 8:
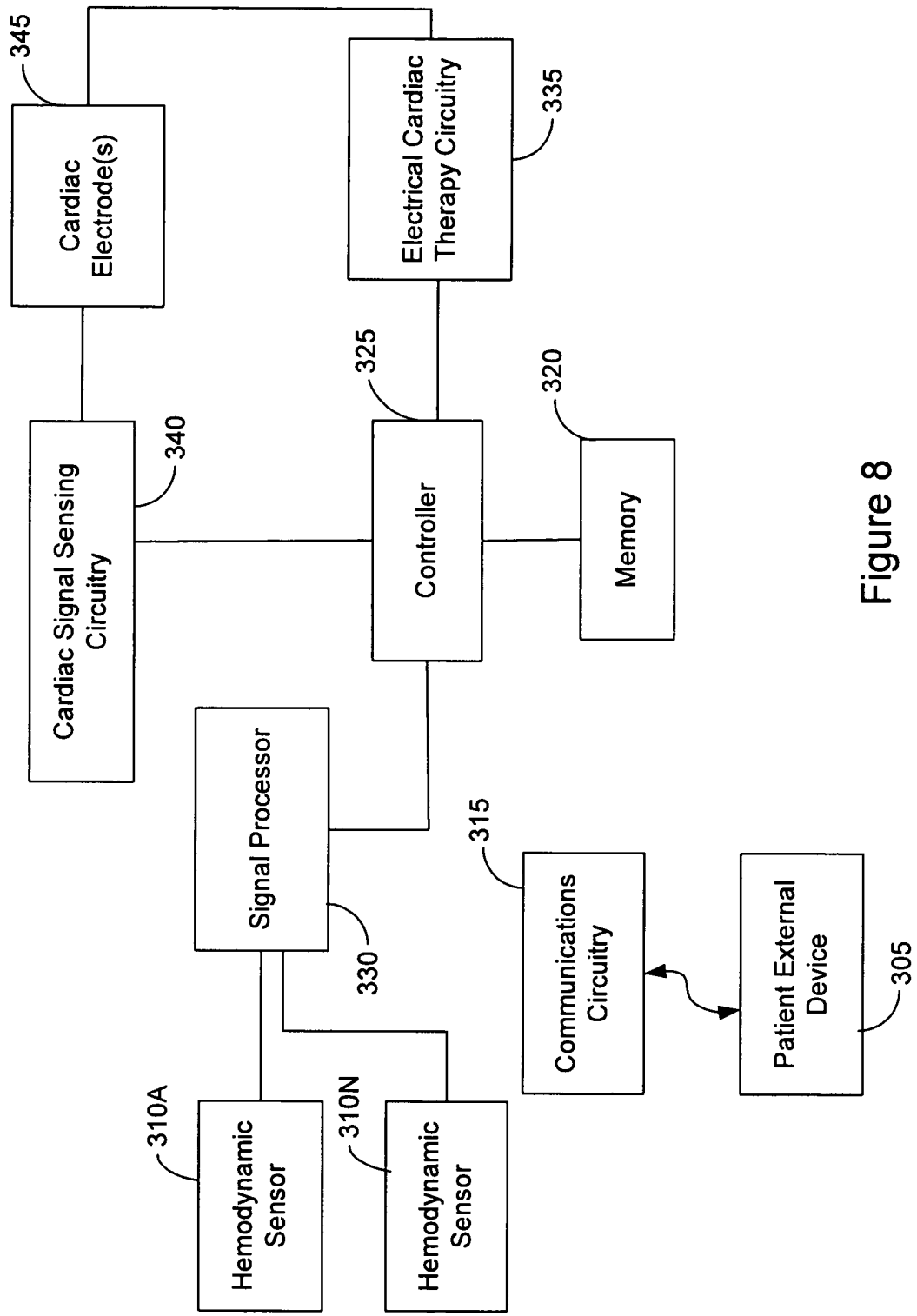
FIG. 8 is a block diagram of circuitry that implements a hemodynamic status assessment methodology in accordance with embodiments of the invention.

FIG. 8 is a block diagram of circuitry that implements a hemodynamic status assessment methodology in accordance with embodiments of the invention. One or more cardiac electrodes 345 may be positioned or disposed at multiple locations on, within, or proximate a heart chamber or vasculature. For example, one or more cardiac leads may support one or more of the cardiac electrodes, and the can or housing of the device may include one or more electrodes useful for sensing cardiac electrical activity (and may also serve as an electrode for energy delivery).

Two or more hemodynamic sensors 310, such as heart sounds sensors for example, are configured to sense hemodynamic signals, and may be the same or different sensor type or sensing modality. Useful sensors 310 include a microphone, accelerometer, and a pressure sensor (e.g., left arterial pressure sensor such as a pulmonary artery pressure sensor, right ventricular pressure sensor), among others. Signals produced by the one or more sensors 310 may be communicated to a signal processor 330, which processes the heart sounds signals for use by a controller 325.

The controller 325 is coupled to the signal processor 330, memory 320, and cardiac signal sensing circuitry 340. In some embodiments, hemodynamic status may be evaluated in accordance with the present invention in a monitoring mode or configuration, in which case electrical cardiac therapy circuitry 335 need not be included. In this regard, embodiments of the present invention may be directed to a diagnostic device that incorporates two or more hemodynamic sensors, such as heart sounds sensors. In other embodiments that provide cardiac electrical therapy, hemodynamic status may be evaluated during arrhythmias and appropriate therapy delivered according to the stability of the arrhythmia using cardiac electrical circuitry 335 in accordance with the present invention.

The memory 320 is configured to store program instructions and/or data. In addition, the stored information may be used to provide a log of events for display or analysis at a later time. The memory 320 may be configured to store the stability threshold, $Th_{CXY}$, which is used by the controller 325 when performing hemodynamic stability assessments, such as by implementing the algorithm shown in FIG. 4. Alternatively, the stability threshold, $Th_{CXY}$, may be stored in the memory of a patient-external device or system, and an external controller may be used to perform hemodynamic stability assessments.

The controller 325 is preferably coupled to communications circuitry 315 which allows the device to communicate with other devices 305, such as a patient-external programmer or advanced patient management system. In some implementations, an advanced patient management (APM) system may be used to collect implanted device data, including hemodynamic signal data, for purposes of evaluating the hemodynamic status of a patient. The APM system or programmer may also be used to implement or facilitate implementation of the hemodynamic status assessment methodology of the present invention. Methods, structures, and/or techniques described herein, may incorporate various APM related methodologies, including features described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Figure 9:
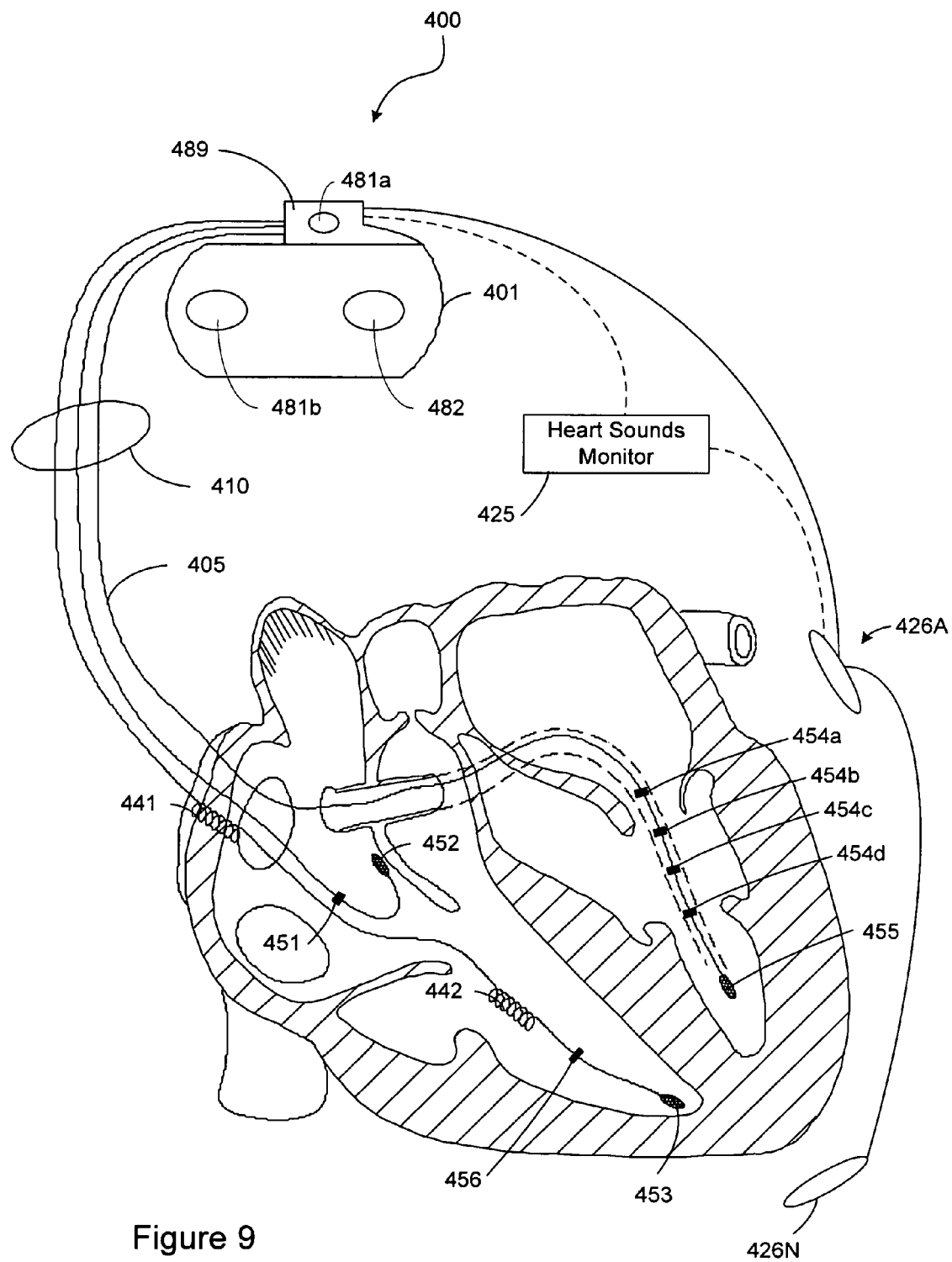
FIG. 9 illustrates a patient-implantable device that may be used in conjunction with a hemodynamic status assessment methodology in accordance with embodiments of the present invention.

FIG. 9 shows an embodiment of the present invention implemented with use of an implanted cardiac therapy device 400. The therapy device 400 includes cardiac rhythm management circuitry enclosed within an implantable housing 401. The CRM circuitry is electrically coupled to an intracardiac lead system 410. Portions of the intracardiac lead system 410 are shown inserted into the patient's heart. The lead system 410 includes cardiac pace/sense electrodes 451-456 positioned in, on, or about one or more heart chambers for sensing electrical signals from the patient's heart and/or delivering pacing pulses to the heart. The intracardiac sense/pace electrodes 451-456 may be used to sense and/or pace one or more chambers of the heart, including the left ventricle, the right ventricle, the left atrium and/or the right atrium. The lead system 410 may include one or more defibrillation electrodes 441, 442 for delivering defibrillation/cardioversion shocks to the heart.

The left ventricular lead 405 incorporates multiple electrodes 454a-454d positioned at various locations within, on or about the left ventricle. Stimulating the ventricle at multiple locations or at a single selected location may provide for increased cardiac output in a patients suffering from HF. In accordance with various embodiments described herein, one or more of the electrodes 454a-454d are selected for pacing the left ventricle. In other embodiments, leads having multiple pacing electrodes positioned at multiple locations within a chamber, such as the one illustrated by the left ventricular lead 405 of FIG. 9, may be implanted within any or all of the heart chambers. A set of electrodes positioned within one or more chambers may be selected. Electrical stimulation pulses may be delivered to the chambers via the selected electrodes according to a timing sequence and output configuration that enhances cardiac function.

Portions of the housing 401 of the implantable device 400 may optionally serve as one or multiple can or indifferent electrodes. The housing 401 is illustrated as incorporating a header 489 that may be configured to facilitate removable attachment between one or more leads and the housing 401. The housing 401 of the therapy device 400 may include one or more can electrodes 481b. The header 489 of the therapy device 400 may include one or more indifferent electrodes 481a.

The housing 401 and/or header 489 may include one or more hemodynamic sensors 482, such as an accelerometer or microphone configured for heart sound sensing. Other types and/or combinations of hemodynamic sensors may be employed. One or more cardiac leads 410 or separate sensor leads may incorporate one or more hemodynamic sensors, such as a pulmonary arterial pressure sensor. In some configurations, one or two extra-cardiac heart sounds sensors 426A-426N may be positioned relative to desired locations of the heart, such as the aorta and apex. Heart sounds sensors 426A-426N may be configured for subcutaneous, extra-thoracic implantation, for example. Heart sounds sensors 426A-426N may alternatively be configured for epicardial fixation.

In accordance with a further embodiment, a heart sounds monitor 425 may be implanted and coupled to heart sounds sensors 426A-426N and the header 489 of the housing 401. The coupling between the heart sounds monitor 425 and the implantable device 400 may be effected through wired or wireless connectivity. The heart sounds monitor 425 may include a processor and other circuitry that implements hemodynamic status assessment in accordance with present invention. The heart sounds monitor 425 may communicate assessment data to the implanted device 400 which may implement an appropriate therapy. In such a configuration, a previously implanted CRM device 400 may be effectively upgraded, with appropriate software updates, to allow for therapy delivery based at least in part on hemodynamic status assessments made by a later-implanted heart sounds monitor 425 in accordance with the present invention.

It is noted that the heart sounds monitor 425 and/or heart sounds sensors 426A-426N may be configured for cutaneous or patient-external deployment, and may communicate with the implanted device 400 or a patient-external system via a wireless link. It is further noted that the heart sounds sensors 426A-426N may be configured for external or internal deployment with or without the need of heart sounds monitor 425. In such a configuration, each of the heart sounds sensors 426A-426N incorporate processing, memory, power, and communications circuitry to facilitate an independent heart sounds sensing capability. Heart sounds data acquired by the independent heart sounds sensors 426A-426N may be wirelessly communicated to the implanted device 400 or a patient-external system, such as a programmer or advanced patient management system, which may implement hemodynamic status assessment algorithms in accordance with the present invention.

The cardiac electrodes and/or other sensors disposed within or on the housing 401 or lead system 410 of the therapy device 400 may produce signals useful for detection and/or measurement of various physiological parameters, such as transthoracic impedance, respiration rate, minute ventilation, heart rate, cardiac dysynchrony, activity, posture, blood chemistry, O2 saturation, heart sounds, wall stress, wall strain, hypertrophy, inter-electrode impedance, electrical delays (PR interval, AV interval, QRS width, etc.), activity, cardiac chamber pressure, cardiac output, temperature, heart rate variability, depolarization amplitudes, depolarization timing, and/or other physiological parameters. It is contemplated that, in certain embodiments, information derived from such signals may be incorporated into the algorithm that is employed to assess hemodynamic status and deliver appropriate therapy based on same. In some configurations, the implantable device 400 may incorporate one or more transthoracic impedance sensors that may be used to acquire the patient's respiratory waveform, and/or to acquire other respiratory-related information. The transthoracic impedance sensor may include, for example, one or more intracardiac electrodes 441, 442, 451-456 positioned in one or more chambers of the heart. The intracardiac electrodes 441, 442, 451-456 may be coupled to impedance drive/sense circuitry positioned within the housing 401 of the therapy device 400. Information from the transthoracic impedance sensor may be used to adapt the rate of pacing to correspond to the patient's activity or metabolic need, among other uses.

Communications circuitry is disposed within the housing 401 for facilitating communication between the CRM circuitry and a patient-external device, such as an external programmer or advanced patient management (APM) system. The communications circuitry may also facilitate unidirectional or bidirectional communication with one or more implanted, external, cutaneous, or subcutaneous physiologic or non-physiologic sensors, patient-input devices and/or information systems.

In embodiments that provide cardiac electrical therapy, the therapy device 400 may include circuitry for detecting and treating cardiac tachyarrhythmia via defibrillation therapy and/or anti-tachyarrhythmia pacing (ATP). Configurations providing defibrillation capability may make use of defibrillation coils 441, 442 for delivering high energy shocks to the heart to terminate or mitigate tachyarrhythmia. In some embodiments, the implantable therapy device 400 may include circuitry for selection of pacing electrode(s), timing sequence, and/or amplitude or pulse waveform output configurations (collectively referred to as pacing output configuration) to be applied via one or multiple electrodes within one or multiple heart chambers.

Hemodynamic status assessment is valuable for optimizing the device therapy for treating tachyarrhythmias. Using hemodynamic signals, such as heart sounds, in accordance with the present invention facilitates exploration of the effect of arrhythmias, and resulting hemodynamic variation, on the spatial relationship between multiple hemodynamic sensors. Compared to hemodynamic sensing based on a single sensor, the present method that uses hemodynamic signals acquired by a multiplicity of spatially separated sensors, such as heart sounds sensors, provides for hemodynamic evaluation that has the potential advantage of less stringent requirements on the signal to noise/interference ratio, as well as bypassing conventional S1/S2 detection and feature extraction processes during arrhythmias, which technically can be very difficult and computationally intensive.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method, comprising:
    sensing, during an event of tachycardia, concurrently by at least two different types of sensors at least two different types of hemodynamic signals, wherein the at least two different types of sensors are located at at least two spatially separated locations within a patient;
    quantifying a spatial relationship between the sensed at least two different types of hemodynamic signals;
    determining a state of patient hemodynamics during the tachycardia event based at least in part on the quantified spatial relationship;
    selecting one or more anti-tachycardia therapies to treat the tachycardia based at least in part on the determined state of patient hemodynamics; and
    delivering the selected one or more anti-tachycardia therapies to treat the tachycardia.

2. The method of claim 1, wherein quantifying the spatial relation comprises quantifying a change in propagation of the sensed hemodynamic signals.

3. The method of claim 1, wherein quantifying the spatial relationship comprises computing a correlation between the sensed hemodynamic signals.

4. The method of claim 1, wherein determining the state of patient hemodynamics during the tachycardia event comprises determining whether the tachycardia event is a stable tachyarrhythmia or an unstable tachyarrhythmia.

5. The method of claim 1, wherein determining the state of patient hemodynamics during the tachycardia event comprises comparing a metric indicative of the quantified spatial relationship to a threshold.

6. The method of claim 5, comprising determining the threshold for a particular patient in relation to the patient's normal sinus rhythm.

7. The method of claim 1, wherein:
determining the state of patient hemodynamics during the tachycardia event comprises determining whether the tachycardia event is a stable tachyarrhythmia or an unstable tachyarrhythmia; and
selecting the one or more anti-tachycardia therapies comprises selecting at least one anti-tachycardia pacing therapy in response to determining that the tachycardia event is a stable tachyarrhythmia, and selecting at least one cardioversion or defibrillation therapy in response to determining that the tachycardia event is an unstable tachyarrhythmia.

8. The method of claim 1, wherein the sensed hemodynamic signals comprise at least two, of a mixed combination, of cardiac impedance signals, cardiac chamber pressure signals, arterial pressure signals, heart sounds, and acceleration signals.

9. A method, comprising:
sensing, during an event of tachycardia, concurrently by at least two different types of sensors at least two different types of hemodynamic signals, wherein the at least two different types of sensors are located at at least two spatially separated locations concurrently within a patient;
quantifying a spatial relationship between sensed at least two different types of hemodynamic signals; and
determining hemodynamic stability of the patient during the tachycardia event based at least in part on the quantified spatial relationship.

10. The method of claim 9, wherein quantifying the spatial relation comprises quantifying a change in propagation of the sensed hemodynamic signals.

11. The method of claim 9, wherein quantifying the spatial relationship comprises computing a cross-correlation, cross-covariance, cross-spectra, coherence, mutual information or cross-entropy between the sensed hemodynamic signals.

12. The method of claim 9, wherein determining hemodynamic stability comprises discriminating between a stable and an unstable state of patient hemodynamics.

13. The method of claim 9, comprising delivering or withholding defibrillation therapy to treat the tachycardia based at least in part on the patient's hemodynamic stability.

14. The method of claim 9, comprising delivering an anti-tachycardia therapy associated with the hemodynamic stability of the patient during the tachycardia event.

15. The method of claim 14, comprising tracking the patient's hemodynamics to assess effectiveness of the anti-tachycardia therapy.

16. The method of claim 9, wherein the sensed hemodynamic signals comprise at least two, of a mixed combination, of cardiac impedance signals, cardiac chamber pressure signals, arterial pressure signals, heart sounds, and acceleration signals.

17. An implantable system, comprising:
at least two different types of implantable hemodynamic sensors adapted for spatially-separated positioning relative to a patient's heart and for sensing hemodynamic signals;
a lead comprising one or more electrodes;
detection circuitry coupled to the lead;
energy delivery circuitry coupled to the lead; and
a processor coupled to the hemodynamic sensors, lead, detection circuitry, and energy delivery circuitry, the processor configured to sense, during an event of tachycardia, at least two different types of hemodynamic signals concurrently from the hemodynamic sensors, quantify a spatial relationship between the at least two different types of sensed hemodynamic signals, and determine a hemodynamic status of the patient during the tachycardia event based at least in part on the quantified spatial relationship, the processor configured to deliver one or more anti-tachycardia therapies associated with the hemodynamic status of the patient.

18. The system of claim 17, wherein the processor is configured to quantify the spatial relation based on a detected change in propagation of the sensed hemodynamic signals.

19. The system of claim 17, wherein the processor is configured to quantify the spatial relationship by computing a correlation between the sensed hemodynamic signals.

20. The system of claim 17, wherein the processor is configured to quantify the spatial relationship by computing a cross-correlation, cross-covariance, cross-spectra, coherence, mutual information or cross-entropy between the sensed hemodynamic signals.

21. The system of claim 17, wherein the processor is configured to discriminate between a stable and an unstable state of patient hemodynamics, and to deliver the one or more anti-tachycardia therapies based on stability of patient hemodynamics.

22. The system of claim 17, wherein the processor is configured to deliver or withhold defibrillation therapy to treat the tachycardia based at least in part on the patient's hemodynamic status.

23. The system of claim 17, wherein the at least two implantable hemodynamic sensors comprise at least two, of a mixed combination, of cardiac impedance sensors, cardiac chamber pressure sensors, arterial pressure sensors, heart sound sensors, accelerometers, and microphones.

* * * * *